(12) United States Patent
Sevinc

(10) Patent No.: US 7,163,394 B2
(45) Date of Patent: Jan. 16, 2007

(54) BALL JOINT FOR A DEVICE USED FOR ACCELERATING JAW GROWTH

(76) Inventor: Habib Sevinc, Schildergasse 112, 50667 Köln (DE)

( * ) Notice: Subject to any disclaimer, the term of this patent is extended or adjusted under 35 U.S.C. 154(b) by 0 days.

(21) Appl. No.: 10/524,949

(22) PCT Filed: Sep. 1, 2003

(86) PCT No.: PCT/EP03/09682

§ 371 (c)(1),
(2), (4) Date: Aug. 1, 2005

(87) PCT Pub. No.: WO2004/024019

PCT Pub. Date: Mar. 25, 2004

(65) Prior Publication Data
US 2006/0040229 A1 Feb. 23, 2006

(30) Foreign Application Priority Data
Sep. 9, 2002 (DE) .......................... 202 13 880 U

(51) Int. Cl.
A61C 3/00 (2006.01)

(52) U.S. Cl. ....................................................... 433/19

(58) Field of Classification Search .................. 433/18, 433/19, 21, 24; 403/114
See application file for complete search history.

(56) References Cited

U.S. PATENT DOCUMENTS

| 2,513,637 | A | * | 7/1950 | Herreshoff et al. | ......... 403/122 |
| 3,798,773 | A | * | 3/1974 | Northcutt | ...................... 433/19 |
| 4,571,110 | A | * | 2/1986 | Amrath | ...................... 403/141 |
| 4,795,342 | A | * | 1/1989 | Jones | ........................... 433/19 |
| 5,378,147 | A | * | 1/1995 | Mihailowitsch | .............. 433/19 |
| 2001/0036614 | A1 | | 11/2001 | Binder | ........................ 433/19 |

FOREIGN PATENT DOCUMENTS

EP 0988835 3/2000

* cited by examiner

Primary Examiner—Cary E. O'Connor
(74) Attorney, Agent, or Firm—Charles L. Schwab; Nexsen Pruet, LLC

(57) ABSTRACT

The invention relates to a ball joint for a device used for accelerating jaw growth, comprising a ball joint head and a ball joint socket that are fastened to the ends of a spring bar and to retaining elements connected to the teeth of the upper jaw and/or of the lower jaw, whereby the ball joint heads and the ball joint sockets are detachably connected to one another, to the spring bar and to the retaining elements.

7 Claims, 2 Drawing Sheets

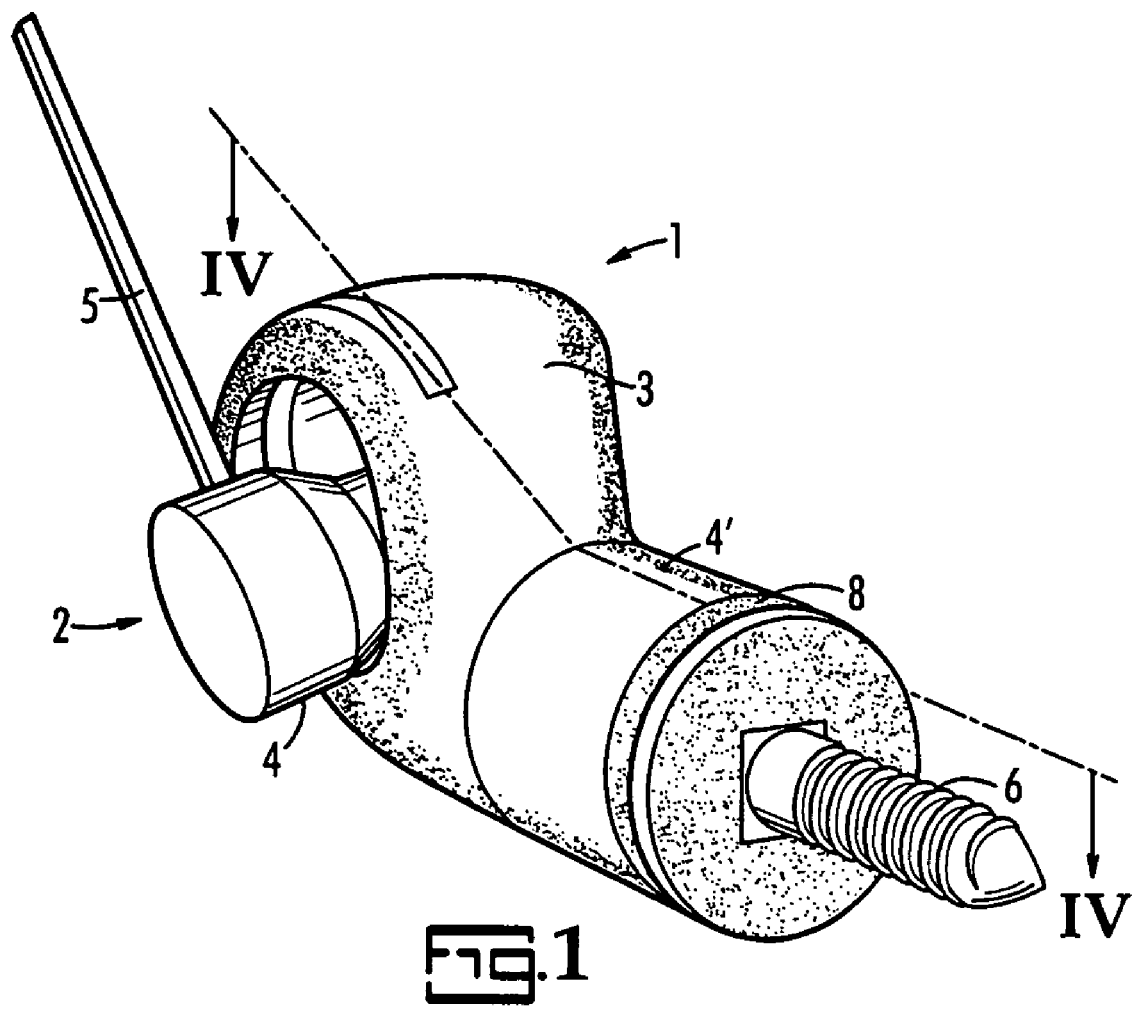

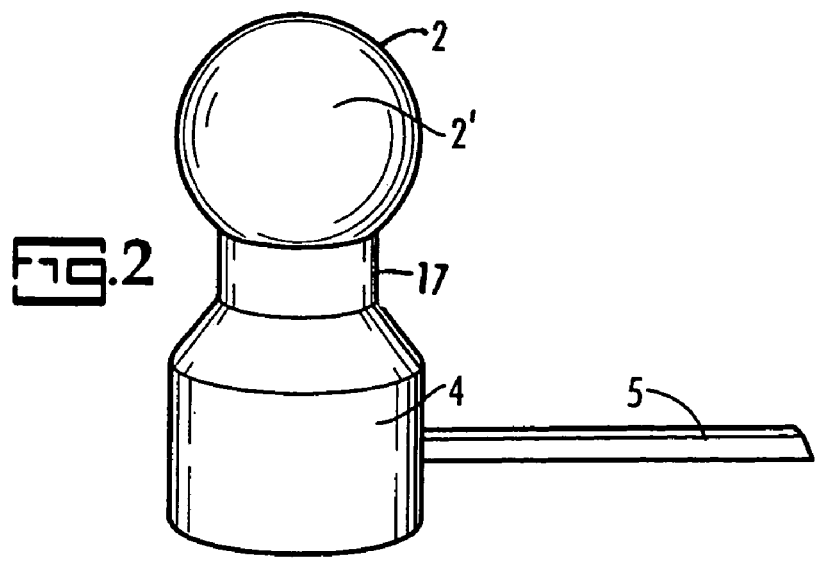
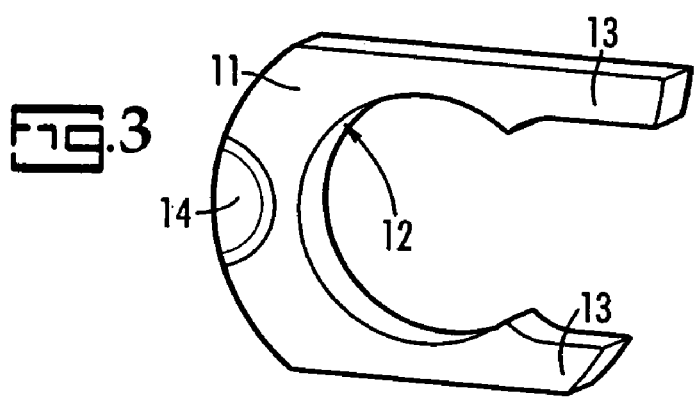
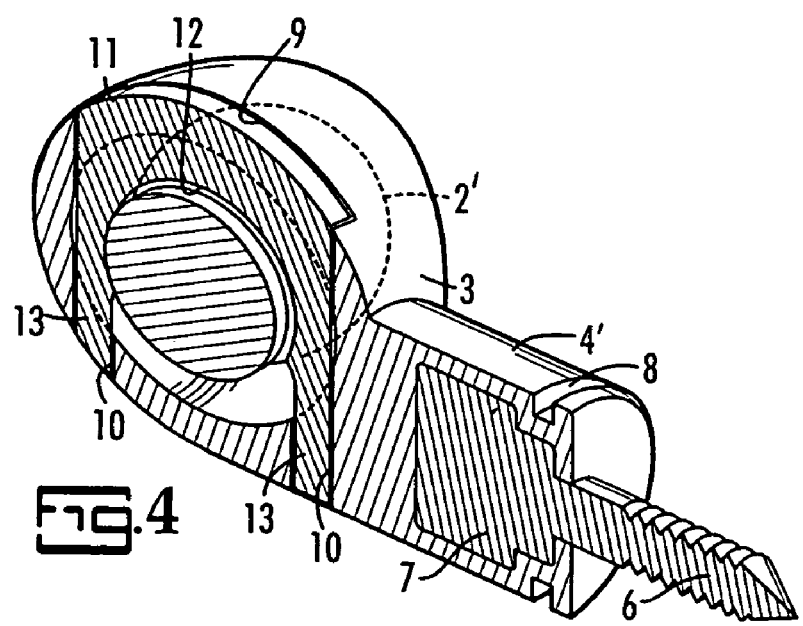

BALL JOINT FOR A DEVICE USED FOR ACCELERATING JAW GROWTH

BACKGROUND OF THE INVENTION

The invention relates to a ball joint for a device used for accelerating jaw growth, having a ball-joint head and an associated ball-joint socket that are fastened to the ends of a spring bar and to retaining elements connected to the teeth of the upper jaw and/or lower jaw.

Such a device for accelerating jaw growth having ball joints is known (DE 19844005 AI). In this known device, the ball-joint sockets are firmly connected to the spring bar and the ball-joint heads are firmly connected to the retaining elements on the teeth. For this reason it is difficult to use this device and to place it fittingly in the mouth of the patient. Further, complete spring bars of various strengths corresponding to the forces provided and, additionally, of unequal lengths must be kept with ball-joint sockets so that they can be employed as needed.

SUMMARY OF THE INVENTION

It is therefore an object of the invention to remedy these disadvantages and to improve the device in such fashion that it can be used in a versatile manner and can be handled easily. Moreover, it is to be easy to vary using simple resources and is to be favorable in respect of manufacturing.

The object of the invention is achieved in that the ball-joint heads and the ball-joint sockets are separably connected to one another and to the spring bar and to the retaining elements. There results a development that makes it possible to fasten the ball-joint heads or ball-joint sockets to the spring bars in arbitrary fashion according to the intended use, both the length and the strength of the spring force of the spring bars being variable. Thus they can be employed invariable fashion as needed. The joints per se are also separably connected to one another, so that the ball-joint heads and the ball-joint sockets can be easily separated from one another. Finally, the ball-joint heads or ball-joint sockets are also separably fastened to the retaining elements connected to the teeth.

In the preceding passages, "ball-joint head(s)" and "ball-joint socket(s)" were mentioned along with one another because the ball-joint heads can be connected both to the retaining elements and, alternatively, to the spring bar, and inversely the ball-joint sockets as well.

This development of the invention yields a simple and variable use of the device for accelerating jaw growth, because arbitrarily long spring bars and spring bars of various spring strengths can be connected to the respective joint halves, because the other joint halves can be fastened to retaining elements in arbitrary fashion and because the joints can in turn be assembled and firmly attached to each other at any time. It should further be pointed out that the retaining elements can be fashioned arbitrarily. Known brackets that are connected to one another with wires can also be used. One of the brackets need only have one fastening capability for a joint part.

For the simple fastening of the ball-joint socket or ball-joint head to the spring bar, these have a screw that is screwed into a hole in the spring core of the spring bar.

The spring core of the spring bar is the element that applies the requisite forces for accelerating the growth of the jaws. For this reason, the pertinent part of the ball joint is appropriately connected to the spring core. To this end the spring core has a fitting hole, which can also be threaded.

Various spring bars of various lengths and various spring strengths, having corresponding holes, can here beamed available as an assortment. It is also possible, however, to furnish spring bars as bar material and to cut these to length and provide them with holes as needed in order to connect them with the screw of the respective half of the ball joint.

The respective ball-joint half, that is, the ball-joint socket or ball-joint head, further have a groove or bead, the groove or bead being connectable to the jacket of the spring bar, which encloses the spring core. To this end the jacket can have, on its inside, a corresponding mating part for connection to the groove orbed of the ball-joint half. This need not be the case, however, because the jacket 3 can also be connected to the groove or bead on the joint half by its stress. The dimensions and the forces are to be fashioned so that a sealing connection is thereby produced between the respective ball-joint half and the jacket, so that no oral fluid can reach the spring core and the screw.

The joint half, that is, the ball-joint socket or ball-joint head, which is connected to the spring bar, advantageously has a preferably cylindrical extension to which the screw is connected, the extension having the groove or bead. In like fashion, of course, the joint part that is connected to the retaining element, that is, the respective ball-joint head or ball-joint socket, can likewise have an extension, which then is also preferably fashioned cylindrical in shape.

For the fastening of the screw to the respective ball-joint half or to the extension, the screw has a head, which is embedded in rotationally and axially fixed fashion in the ball-joint part or the extension.

The ball-joint part that is connected to the retaining element has a bar, preferably at a right angle to the longitudinal axis of this ball-joint part, for separable connection to the retaining element. For the accommodation of the baron the respective retaining element or on the bracket, at least one tubular lug is fastened there in each case, the aperture of which lug matches the cross-sectional measure of the bar. In this way, a simple and rapid fastening can be achieved by simply inserting the rod with the respective ball-joint part into the lug. Depending on the arrangement of the spring bar in the mouth of the patient, inserting the bar 4 into the lug is sufficient to fasten the device, so that no special securing of the bar in the lug is necessary. It is, however, immediately possible to fasten the bar in the lug, the simplest approach being to bend the bar around the end of the lug opposite to the ball-joint part.

Both the bar and the inner side of the lug can have a polygonal, preferably rectangular or square, cross section, so that the ball-joint part is again secured in the rotational direction about the longitudinal axis of the bar. This is important particularly when the spring bar is arranged between the upper jaw and the lower jaw, because in this way the position of the ball-joint head in the ball-joint socket can be defined so that there is no jamming of the ball joint.

For the separable connection of the ball-joint head to the ball-joint socket and its securing, there is proposed a securing device that includes a securing slide and a slot-like recess matching it in the ball-joint socket. The securing slide is preferably fork-like in shape, and the middle portion of the fork has a cavity matched to the corresponding part of the ball-joint head. This middle part thus preferably has a surface that corresponds to a part of a ball-joint socket, which naturally only partly encloses the ball-joint head, because the fork-like opening in the securing slide must engage behind the ball-joint head. The slot-like recess in the ball socket is advantageously provided with two openings on the opposite side of the socket opening, into which openings the fork ends of the securing slide are fitted. In this way, firm retention of the securing slide in the slot-like recess and in the two openings for the fork ends is achieved. In the region opposite to the fork 5 shaped end, the securing slide can further have a notch, recess or the like, which serves to facilitate handling of the securing slide with a tool.

BRIEF DESCRIPTION OF THE DRAWINGS

For the further explanation of the invention, reference is made to the drawings illustrating an exemplary embodiment of the invention, in which:

FIG. 1 is a perspective overall view of a ball joint;
FIG. 2 is a lateral view of a ball-joint head;
FIG. 3 is a perspective lateral view of a securing slide; and
FIG. 4 is a section through a ball-joint socket along the line IV—IV in FIG. 1.

DETAILED DESCRIPTION OF THE INVENTION

In FIGS. 1 to 4, insofar as illustrated in particular, reference character 1 identifies a ball joint having a ball-joint head 2 and a ball-joint socket 3. The ball-joint head 2 and ball-joint socket 3 have extensions 4 and 4', respectively which are preferably fashioned cylindrical in shape and are molded onto the ball-joint head or respectively the ball-joint socket.

Fastened to prolongation 4 of ball-joint head 2 is a bar 5 that has a rectangular cross section. This bar 5 can, as explained in the general specification, be inserted into lugs that are fastened to retaining elements or brackets fastened to the teeth of the upper jaw or lower jaw of the patient, so that the ball-joint head is firmly retained on the retaining element or bracket. If necessary, bar 5 can be secured in the lug in simple fashion by bending the free end of the bar slightly after insertion into the lug.

As can be inferred from FIGS. 1 and 4, a screw 6 is inserted in extension 4' of ball-joint socket 3, which screw is inserted in extension 4' in rotationally and axially fixed fashion by its head 7. The ball-joint socket is connected with this screw to a spring bar, not illustrated, the screw being screwed into a hole or opening in the spring core of the spring bar. The cylindrical extension 4 of ball-joint socket 3 has a radially outward open annular groove 8, which can be put into effective connection with a jacket of the spring bar. To this end the jacket has on its inner surface a bead, which snaps into the groove, or the jacket is elastic and is so dimensioned that it penetrates partly into the groove when slid onto the extension and in this way a sealing connection is produced.

As can further be inferred from FIGS. 1 and 4, the ball-joint socket has a slot-like recess 9 in the prolongation of which there are two parallel openings 10.

In FIG. 3, reference character 11 identifies a securing slide, which is fashioned in fork shape. Securing slide 11 has, in the middle region, identified by reference character 12, a recess 17 that is matched to the ball 2' of ball-joint head 2 so that the ball 2' of ball-joint head 2 is secured in ball-joint socket 3 after the securing slide is inserted into slot-like recess 9. Here fork ends or tines 13 of securing slide 11 reach into openings 10 of the ball-joint socket and brace themselves there. Further made on securing slide 11 is a notch 14 with whose aid the securing slide can be removed from the ball-joint socket. The fork tines or ends 13 of the securing slide 11 straddle a reduced diameter annular recess 17 in the cylindrical prolongation 4, which recess 17 is adjacent the ball 2' and has a smaller diameter than the ball 2'. Thus the tines 13 of the slide 11 straddle the reduced diameter portion or recess 17, when installed as shown in FIG. 4, and serve to maintain the ball 2' in the socket 3.

The invention claimed is:

1. In a device for accelerating jaw growth of the type having a spring bar and retaining elements connected to the teeth of at least one of the upper and lower jaws, a ball joint comprising:
   a ball-joint socket,
   a ball-joint head rotatably secured in said ball-joint socket, said ball-joint head being adapted for separatable connection to said retaining elements, and
   a cylindrical extension on said ball-joint socket said cylindrical extension having a radially outward open, annular groove facilitating connection to said spring bar.

2. The device of claim 1 including a screw axially and rotationally fixed in said cylindrical extension, said screw being adapted for connection to said spring bar.

3. The device of claim 1 wherein said ball joint head includes a ball and a cylindrical prolongation and further comprising a securing device for maintaining said ball in said ball-joint socket including a slot like recess in said ball joint socket and a fork shaped securing slide in said recess with tines straddling said cylindrical prolongation.

4. The device of claim 3 wherein said securing slide includes a middle region matches the spherical surface of the ball-joint head.

5. The device of claim 4 wherein two parallel openings are formed in said ball joint socket in alignment with opposite sides of said slot-like recess and wherein said tines extend, respectively, into said parallel openings.

6. The device of claim 4 including a screw axially and rotationally fixed in said cylindrical extension, said screw being adapted for connection to said spring bar.

7. In a device for accelerating jaw growth of the type having a spring bar and retaining elements connected to the teeth of at least one of the upper and lower jaws, a ball-joint comprising:
   a ball-joint head including a ball and a cylindrical prolongation with an annular recess adjacent said ball, said ball-joint head being adapted for connection to said retaining elements,
   a ball joint socket adapted for connection to said spring bar, said ball-joint socket rotatably supporting said ball and including
   a slot like recess at one side of said socket and a pair of parallel openings aligned with said recess at the side of said socket opposite said one side, and
   a fork shaped securing slide in said slot like recess including a pair of tines extending into said pair of openings, respectively, said tines straddling said cylindrical prolongation and being disposed in said recess thereby maintaining said ball-joint head assembled with said ball-joint socket.

* * * * *